United States Patent [19]

Moore et al.

[11] 3,952,047

[45] Apr. 20, 1976

[54] METHOD OF PURIFYING PYRETHRUM EXTRACT

[75] Inventors: Joseph B. Moore, Edina; Dean C. Kassera, St. Louis Park, both of Minn.

[73] Assignee: McLaughlin Gormley King Company, Minneapolis, Minn.

[22] Filed: Jan. 11, 1974

[21] Appl. No.: 432,656

[52] U.S. Cl. .......... 260/468 H
[51] Int. Cl.[2] .......... C07C 67/48
[58] Field of Search .......... 260/468 H

[56] References Cited

UNITED STATES PATENTS 3,042,706 7/1962 Haus et al. .......... 260/468

OTHER PUBLICATIONS

Merck Index, 8th Ed., pp. 8, 671, (1968).

*Primary Examiner*—Robert Gerstl
*Attorney, Agent, or Firm*—Dorsey, Marquart, Windhorst, West & Halladay

[57] ABSTRACT

A method of purifying crude pyrethrum extract through the use of acetonitrile as the extracting agent comprising the method steps of mixing crude pyrethrum extract with acetonitrile, separating the acetonitrile-pyrethrum extract layer at a temperature effective to precipitate out undesirable impurities and waxes in such acetonitrile-pyrethrum extract, removing the acetonitrile by distillation, mixing the concentrated pyrethrum extract with an amount of mineral spirits effective to precipitate out undesirable impurities, and removing the mineral spirits by distillation.

12 Claims, No Drawings

METHOD OF PURIFYING PYRETHRUM EXTRACT

BACKGROUND AND SUMMARY OF THE INVENTION

The present invention relates generally to an improved method of purifying crude pyrethrum extract and more specifically to a method of purifying crude pyrethrum extract through the use of acetonitrile (methyl cyanide) as the extracting agent.

Pyrethrum is one of the oldest and most widely used insecticides primarily because of its effectiveness against a wide variety of insects and because of its relatively low degree of toxicity to humans and animals. Further, unlike many other insecticides, pyrethrum does not appear to induce resistance in insects which are exposed to a sublethal dose of the same.

Crude pyrethrum extract is normally manufactured by solvent extraction or treatment of dry pyrethrum flowers to form a crude pyrethrum extract. There are essentially two methods currently in use to accomplish such extraction. One is percolation with petroleum ether in a batch system. The other is a continuous flow system in which a countercurrent extraction system is utilized. In some areas, this crude extract is centrifuged to remove some of the heavier solids whereas, in other areas, a process is used to standardize the crude extract to 25% by the addition of a petroleum solvent such as deodorized kerosene. This crude extract as shipped is a dark viscous oleoresin and usually contains from 25% to 40% pyrethrins. Such crude extract also includes relatively large amounts of impurities such as colored extractives, resins, fatty acids and the like, which, among other things, render the eventual refined extract undesirable from a color standpoint if not removed and cause such refined extract to lack stability. To a certain extent, these impurities precipitate out when the extract is diluted with deodorized kerosene to usable concentrations; however, a large percentage of the impurities remain in the crude extract after such dilution.

The subject matter of the present invention relates to an improved process to further refine this crude pyrethrum extract to a concentrated refined pyrethrum extract which can be readily used and is desirable to use in the preparation of, among other things, insecticides. It is highly desirable to obtain such a refined extract with little or no unsaturated fatty acids since such fatty acids tend to react with metals such as iron, cadmium, copper, zinc and lead to form insoluble precipitates. The fatty acids also tend to oxidize and form peroxides which in turn degrade the pyrethrins in storage. It is also desirable to have a more efficient refining process which provides an improved quality of refined pyrethrum. Finally, it is desirable to provide a refined extract with improved color quality to prevent staining of fabrics and the like when the refined extract is used as an ingredient in insecticides.

The present invention provides for the purification or refining of crude pyrethrum extract through the use of acetonitrile as the extracting agent and includes the following steps: Extracting the crude pyrethrum which constitutes approximately 25% to 40% pyrethrins with acetonitrile (methyl cyanide); allowing the mixture to separate and drawing off the solvent extract layer at a temperature sufficiently low to satisfactorily remove the waxes and various other precipitates remaining in the solvent extract and formed as a result of the reduced temperature; removing the resulting solid particles by filtration and removing the acetonitrile by distillation; diluting the recovered pyrethrum extract with mineral spirits such as a light isoparaffinic solvent and adding decolorizing activated carbon to this solution to remove unwanted color bodies; filtering the solid particles from this resulting solution; and distilling the solution to remove the mineral spirits. The resulting product is a refined pyrethrum extract useable in, among other things, the manufacture of insecticides.

Accordingly, it is an object of the present invention to provide an improved method of refining crude pyrethrum which produces a higher quality refined pyrethrum extract.

Another object of the present invention is to provide a method of refining crude pyrethrum extract through the use of acetonitrile (methyl cyanide).

A further object of the present invention is to provide a method for refining crude pyrethrum extract to produce a refined extract having a color quality which is improved over prior methods.

Another object of the present invention is to provide a method for refining crude pyrethrum extract to produce a refined extract having improved stability and an improved yield over prior methods.

Another object of the present invention is to provide a method for refining crude pyrethrum extract in which a refined extract is produced which is free of impurities which might precipitate out upon standing for an extended time.

These and other objects of the present invention will become apparent with reference to the description below of the preferred method and to the appended claims.

DESCRIPTION OF THE PREFERRED EMBODIMENT

The first step in the improved method of the present invention involves extracting a volume of crude pyrethrum extract by mixing acetonitrile (methyl cyanide) with such crude extract. The primary purpose of this initial extraction step is to recover all of the pyrethrins which are soluble in the acetonitrile while excluding as many of the resins, waxes and other impurities as possible. Although a variety of concentrations and purities of acetonitrile may work satisfactorily in the present process, the inventors have found it preferrable to use virtually pure acetonitrile such as that identified as acetonitrile (PM 2118) which is manufactured by Eastman Chemical Products, Inc. of Kingsport, Tennessee. This initial extraction step is carried out on a crude pyrethrum extract which normally consists of approximately 25% to 40% pyrethrins, however, applicants have found it desirable, especially when working with more concentrated crude pyrethrum extract, to dilute the extract with a petroleum distillate such as deodorized kerosene. This dilution reduces the viscosity of the crude extract and provides a more efficient extraction. This mixture of crude pyrethrum extract and acetonitrile is then agitated and allowed to separate out into a layer of acetonitrile-pyrethrum extract containing acetonitrile and dissolved pyrethrins and a layer of remaining crude pyrethrum extract containing the undissolved pyrethrins and undissolved waxes and other impurities. The inventors have found that an agitation time of between 15 and 30 minutes is sufficient to provide acceptable contact between the crude extract and the acetonitrile. Following the agitation step, the mixture i allowed to separate, after which the solvent layer (acetonitrile-pyrethrum extract) is drawn off and recovered. As discussed below, this separation step may be carried out at room temperature, at which time the recovered extract is then chilled, or the separation step may be carried out at a low temperature thus avoiding the chilling step.

It is preferrable for the initial extraction process to include additional successive extractions of the remaining crude pyrethrum extract with smaller proportions of acetonitrile. Although the ratio of acetonitrile to crude extract necessary to produce satisfactory results may vary in the extraction step discussed above, the inventors have found, as shown in the Examples I and II below that a satisfactory extraction of crude pyrethrum extract may be obtained with an acetonitrile to crude pyrethrum extract ratio of ten to one (Example I) and an acetonitrile to crude pyrethrum extract ratio of five to one (Example II). More specifically, in Example I, 50 grams of crude pyrethrum extract was initially extracted with 125 ml of acetonitrile followed by four successive extractions of the remaining crude extract, three of which were accomplished with 100 ml portions of acetonitrile and the last of which was accomplished with a 75 ml portion. In Example II, 50 grams of crude pyrethrum extract was initially extracted with 100 ml of acetonitrile followed by three successive extractions of the remaining crude pyrethrum extract of 50 ml each. The inventors found, however, that in Example II, the final extraction with 50 ml of acetonitrile was necessary in order to obtain commercially acceptable recovery of refined extract. Thus, the inventors believe that the extraction or refining of crude pyrethrum extract with acetonitrile must be accomplished with at least a 5 to 1 ratio of acetonitrile to crude pyrethrum extract in order to obtain adequate recovery. The minimum ratio necessary of course would depend to some extent on the quality of the initial crude extract and various other factors. Although purification and refinement can be accomplished with an acetonitrile to crude extract ratio lower than this minimum ratio, the recovery of the refined pyrethrins would be significantly reduced.

Following the extraction process discussed above, the acetonitrile extracts obtained from each of the initial and successive extractions are combined and chilled. The purpose of such chilling step is to solidify and precipitate out the waxes and other solid substances which are in solution with the acetonitrile at higher temperatures. The exact temperature to which the combined extracts are chilled is not critical; however, the temperature must be sufficiently low to be effective to precipitate the waxes and other impurities that are desired to be removed during this step. The inventors have found that chilling the combined extracts to a temperature of −4° F. accomplishes the precipitation of the various waxes and other impurities satisfactorily. Chilling to a temperature above or below −4° F. has no effect on the total purifying or refining process other than the effect that it may have on the amount of waxes and other impurities which it precipitates out. While the combined extracts are still chilled, they are filtered to remove the precipitated waxes and other impurities. The mesh size of the filter or the particular filtering process is not critical as long as such filtering process is effective to remove the waxes and other solid impurities from the solution. As pointed out briefly above, the chilling and filtering of the combined extracts need not be a separate step but may be combined with the extraction step by chilling each of the mixtures of crude extract and acetonitrile prior to separating the acetonitrile extract layer from the dilute crude extract layer.

Following the chilling and filtering step, the acetonitrile is removed from the acetonitrile extract solution by distillation. The inventors have found through their experimentation that the distillation of the refined extract solution to remove the acetonitrile takes place between 50° and 70° centigrade and that such distillation may be accomplished at about 50° centigrade with the aid of a vacuum. The concentration of the refined pyrethrum following this distillation step ranges from 45% to 60%, depending primarily on when the distillation is stopped. Although most of the impurities are removed from the refined extract at this stage in the process, the inventors have found it preferrable to dilute the concentrated pyrethrum extract which is recovered from the distillation step with relatively low boiling mineral spirits such as a light isoparaffinic solvent to precipitate out any resins which may remain in the refined extract. Although a variety of solvents may be used, the inventors have found that a solvent identified by the trade name "Soltrol 130" which is manufactured and sold by Phillips Petroleum Company of Bartellsville, Oklahoma, is acceptable for this purpose. The inventors have also found it satisfactory to dilute the refined extract to approximately 2% pyrethrins. Although such percentage is not critical, the dilution should be sufficient to kick out the unwanted resins and other remaining impurities. At this same time, a quantity of decolorizing activated carbon may be added to the diluted solution to remove the color bodies (usually the larger molecules) by absorption to decolorize the diluted solution. In the preferred method, the inventors have used about eight grams of activated carbon known by the trade name "Darco G-60" which is manufactured and sold by Atlas Chemical Industries, Inc. of Wilmington, Delaware. The amount of activated carbon which is added, of course, depends upon the decolorization desired. Generally, the better color quality that is desired, the more activated carbon which must be added. However, the addition of too much activated carbon may affect the final recovery of the pyrethrins. If the color of the final pyrethrum extract is not important to the user of this method, the quantity of activated carbon added may be reduced or eliminated entirely.

Following dilution of the refined extract and the addition of the activated carbon for decolorization, the resulting mixture is agitated for approximately two hours and filtered. Although the agitation time is not critical, it must be sufficiently long to allow adequate contact to be made between the diluted extract and the activated carbon. In the preferred application of the present method, the inventors have found that an agitation time of approximately two hours is sufficient. The agitation time for any particular application of the present method, however, may depend on the quality and type of crude pyrethrum extract used and the equipment which is used in agitation.

Following the filtration of the diluted pyrethrum extract, the mineral spirit solvent is removed by distillation under a vacuum of approximately one mm. of mercury. In the preferred method using "Soltrol 130" solvent, this distillation is accomplished at approximately 70° to 80° centigrade. Following the distillation step, the resulting solution has a pyrethrum concentration of approximately 40% to 45%.

At this point, the refining of the crude pyrethrum extract according to the present invention is complete; however, the refined extract is preferrably standardized by diluting such extract to a concentration of 20% pyrethrins with a petroleum distillate or other acceptable diluent. In the preferred method, the inventors accomplish such dilution with deodorized kerosene.

Without being limiting, the following examples serve to illustrate the refining of crude pyrethrum extract with the process of the present invention.

EXAMPLE I

50 Grams of a crude pyrethrum extract having a pyrethrum concentration of 30% was mixed with 125 ml of acetonitrile and allowed to separate. The solvent layer (acetonitrile-pyrethrum extract) was then drawn off and the remaining crude pyrethrum extract was extracted again with 4 successive portions of acetonitrile, the first 3 portions being 100 ml each and the final portion being 75 ml. Thus, the 50 grams of crude pyrethrum extract was extracted with a total of 500 ml of acetonitrile which constitutes a ratio of approximately one part crude pyrethrum extract to ten parts of acetonitrile solvent. In this example, the acetonitrile used was acetonitrile (PM 2118) purchased from Eastman Chemical Products, Inc. of Kingsport, Tennessee. The acetonitrile extracts of the five extractions were then combined together and chilled to −4° F. to precipitate out the waxes and various other substances in the solution. The chilled extract was then filtered in a chilled state, removing the waxes and other solid substances formed during the chill step. The filtered acetonitrile extract was then distilled between a temperature range of from 50° to 70° centigrade with vacuum to remove the acetonitrile. The concentrated pyrethrum extract was next diluted to approximately 2% pyrethrins with a light isoparaffinic solvent ("Soltrol 130" manufactured and sold by the Phillips Petroleum Company of Bartellsville, Oklahoma). At the same time, eight grams of a decolorizing activated carbon ("Darco G-60" manufactured and sold by Atlas Chemical Industries, Inc. of Wilmington, Delaware) was added. The diluted solution was mixed for approximately two hours and filtered. The isoparaffinic solvent was removed by distillation under vacuum of approximately one mm. of mercury at temperatures between 70° and 80° centigrade. The remaining pyrethrum extract was then diluted to approximately 20% pyrethrins with deodorized kerosine to standardize the final product. The recovered extract was analyzed for pyrethrin content and the results showed a complete recovery of pyrethrins (100.2% yield) in the extraction process. When tested for color, the 20% refined extract showed a Gardner-Holt color of nine, a considerable improvement over the typical color of eleven obtained by other processes.

EXAMPLE II

This example was used, among other things, to establish guidelines for the minimum limit of acetonitrile necessary for complete extraction of pyrethrins from the crude extract. In this example, 50 grams of crude pyrethrum extract was extracted initially with 100 ml of acetonitrile. The acetonitrile-pyrethrum extract layer was drawn off and the remaining crude pyrethrum extract was exposed to three successive extractions of 50 ml each. It was found that the last 50 ml portion was necessary in order to completely remove the pyrethrins from the crude pyrethrum extract as indicated by a qualitative test for pyrethrins in the remaining wax residues. Thus, in Example II, the 50 grams of crude extract was extracted with a total of 250 ml of acetonitrile which constitutes one part crude extract to five parts of acetonitrile. The acetonitrile extracts were then combined, chilled to −4° F. and filtered while chilled. After filtration, the acetonitrile was removed by distillation with the aid of a vacuum at temperatures between 50° and 70° centigrade. A light isoparaffinic solvent ("Soltrol 130") was added to the concentrated extract so that the resulting solution contained approximately 2% pyrethrins. Eight grams of a decolorizing activated carbon ("Darco G-60") was also added to the solution at this time and the total solution was then mixed for approximately 2 hours and filtered. The isoparaffinic solvent was removed under vacuum at temperatures between 70° and 80° centigrade. The refined pyrethrum extract was then standardized by dilution to approximately 20% pyrethims with deodorized kerosene. Upon testing, the final extract had a Gardner-Holt color of approximately nine as compared to a typical eleven obtained by other refining processes. The analysis of the pyrethrum content showed a recovery value of approximately 100.6% for the extraction process.

The results obtained from the above example show that the refining of crude pyrethrum extract with the present process gives an improved, more highly refined product with a much improved color. Other tests have shown that the quality of the refined product is further improved in that there are additional inactive constituents of the crude pyrethrum extract removed by the present process. Qualitative tests indicate that there is a greater removal of fatty acids by this process than there are with other prior processes. Also, tests have led the inventors to believe that the present process accomplishes the removal of taraxasterol from the crude pyrethrum extract. By removal of this material, an improved extract is obtained in that there is little tendency for crystaline percipitate to form on standing. Other tests show that the removal of additional fatty acids results in improved pyrethrum stability of the refined extract.

Although the description of the preferred method and the examples herein have been quite specific, it is contemplated and understood that various changes and modifications may be made to the preferred method without departing from the spirit and scope of the present invention. Consequently, the inventors intend that the specific description and examples should be illustrative only and that the scope of the present invention should be dictated by the appended claims rather than by the description of the preferred method or examples.

We claim:

1. A process for purifying crude pyrethrum extract formed by the extraction of pyrethrum flowers with an appropriate solvent and containing a mixture of pyrethrins and various impurities, said process comprising:

mixing a crude pyrethrum extract with virtually pure acetonitrile and allowing the same to separate into an acetonitrile-pyrethrum extract layer and a remaining crude pyrethrum extract layer;

chilling said acetonitrile-pyrethrum extract and remaining crude pyrethrum extract layers to a temperature effective to precipitate out waxes and other undesirable impurities in said mixture;

removing the acetonitrile-pyrethrum extract layer;

removing the acetonitrile from the acetonitrile-pyrethrum extract by distillation to form a concentrated pyrethrum extract, said distillation being carried out at the distillation temperature of acetonitrile;

diluting said concentrated pyrethrum extract with a volume of mineral spirits effective to precipitate out remaining undesirable impurities; and removing the mineral spirits by distillation and separating said remaining precipitated impurities.

2. The method of claim 1 wherein said mixture of crude pyrethrum extract and virtually pure acetonitrile is chilled to a temperature of about −20° C.

3. The method of claim 1 wherein the acetonitrile is removed from the acetonitrile extract by distillation at a temperature between 50° and 70° C. under vacuum.

4. The method of claim 1 wherein said concentrated pyrethrum extract is diluted with mineral spirits to approximately 2% pyrethrins.

5. The method of claim 1 wherein the mineral spirits have a boiling point enabling the same to be removed from the pyrethrum extract by distillation at a temperature at between 70° and 80° C. under vacuum of approximately 1 mm. of mercury.

6. The method of claim 5 wherein the mineral spirits comprise a light isoparaffinic solvent.

7. The method of claim 1 including mixing activated carbon with said concentrated pyrethrum extract in an amount effective to remove undesirable color bodies therefrom.

8. The process of claim 1 including standardizing the resulting pyrethrum extract by adding a petroleum distillate.

9. The process of claim 8 wherein such petroleum distillate is deodorized kerosene.

10. The method of claim 1 including mixing said remaining crude pyrethrum extract with at least 1 additional volume of acetonitrile and after each such mixture, separating the resulting acetonitrile-pyrethrum extract layer at a temperature effective to precipitate out waxes and other undesirable impurities.

11. The method of claim 10 including combining the acetonitrile-pyrethrum extract resulting from each of the mixtures of remaining crude pyrethrum extract and acetonitrile prior to removing the acetonitrile from such acetonitrile-pyrethrum extract by distillation with vacuum.

12. The method of claim 11 wherein the ratio of total acetonitrile to the crude pyrethrum extract is at least 5 to 1.

* * * * *